US006401722B1

(12) United States Patent
Krag

(10) Patent No.: US 6,401,722 B1
(45) Date of Patent: Jun. 11, 2002

(54) METHOD FOR STABILIZING AND REMOVING TISSUE

(75) Inventor: David N. Krag, Shelburne, VT (US)

(73) Assignee: Calypso Medical Technologies, Inc., Seattle, WA (US)

( * ) Notice: Subject to any disclaimer, the term of this patent is extended or adjusted under 35 U.S.C. 154(b) by 0 days.

(21) Appl. No.: 09/442,793

(22) Filed: Nov. 18, 1999

Related U.S. Application Data

(62) Division of application No. 09/096,807, filed on Jun. 12, 1998, now Pat. No. 6,015,390.

(51) Int. Cl.$^7$ .............................................. A61B 19/00
(52) U.S. Cl. ........................... 128/898; 606/21; 606/23
(58) Field of Search ............. 606/20–26; 128/DIG. 27, 128/898; 600/547, 549

(56) References Cited

U.S. PATENT DOCUMENTS

| | | | | |
|---|---|---|---|---|
| 4,306,568 A | * | 12/1981 | Torre .......................... 600/547 |
| 4,327,733 A | * | 5/1982 | Gallie .......................... 606/21 |
| 4,399,441 A | | 8/1983 | VaughAn et al. |
| 4,802,475 A | * | 2/1989 | Weshahy ...................... 606/21 |
| 5,108,390 A | | 4/1992 | Potocky et al. |
| 5,250,944 A | | 10/1993 | Urbas et al. |
| 5,252,962 A | | 10/1993 | Urbas et al. |
| 5,262,772 A | | 11/1993 | Urbas et al. |
| 5,420,579 A | | 5/1995 | Urbas et al. |
| 5,481,262 A | | 1/1996 | Urbas et al. |
| 5,519,381 A | | 5/1996 | Marsh et al. |
| 5,531,742 A | | 7/1996 | Barken |
| 5,628,771 A | | 5/1997 | Mizukawa et al. |
| 5,724,030 A | | 3/1998 | Urbas et al. |
| 6,015,390 A | * | 1/2000 | Krag .......................... 600/549 |
| 6,142,991 A | * | 11/2000 | Schatzberger ................ 606/21 |

OTHER PUBLICATIONS

Brochure: Discover new peaks in Cryosurgical precision and efficiency. By ENDOcare, Inc., Jan., 1997.

* cited by examiner

Primary Examiner—Michael Peffley
(74) Attorney, Agent, or Firm—Perkins Coie LLP

(57) ABSTRACT

A method of stabilizing a tissue mass, using a system (8) that includes temperature sensors (10), a scanner (80), and a cryoprobe (220). The sensors provide temperature information with respect to a tissue portion adjacent thereto. The sensors include an identification (ID) code and an ID decoder. The ID decoder compares the sensor ID code to an ID code contained in an interrogation signal provided by the scanner. If the codes match, the sensor transmits the temperature information to the scanner, which processes and displays the temperature information in a humanly recognizable form. The method includes the step of inserting a cryoprobe into a tissue volume to be stabilized so that a portion of the cryoprobe projects therefrom. Then, the tissue volume is frozen while monitoring the size or temperature of the tissue volume. Freezing is terminated when the tissue volume is frozen (or reaches a first temperature level), and then removed while grasping the cryoprobe so as to stabilize the tissue volume.

7 Claims, 11 Drawing Sheets

METHOD FOR STABILIZING AND REMOVING TISSUE

PRIOR APPLICATION INFORMATION

This is a divisional application of U.S. patent application Ser. No. 09/096,807, filed Jun. 12, 1998 now U.S. Pat. No. 6,015,390.

FIELD OF THE INVENTION

The present invention relates to a method of stabilizing a tissue mass, e.g., a breast tumor or lesion, using a cryoprobe for freezing and stabilizing the tissue, with one embodiment of the method involving the use of temperature sensors and a scanner for determining the temperature of the sensors.

BACKGROUND OF THE INVENTION

A current technique for performing an excisional biopsy of a non-palpable breast lesion that has been identified by mammogram or other method involves placement of a needle or guide wire (e.g., a "Kopanz wire"), with or without blue dye, to guide the surgeon to the lesion.

The tip of the needle is generally placed directly in or as close as possible to the lesion. When larger or more complex lesions are encountered, two or more guide wires are sometimes placed at each edge of the lesion. The entry point of the needle through the skin of the breast is usually several centimeters from the lesion due to the logistics of needle placement. The surgeon does not cut along the shaft of the needle from the skin because the distance is too great. Instead, the surgeon must estimate where in the breast the lesion is located by making reference to the location of the needle.

This technique is not optimal. Due to the amorphous and highly pliable nature of certain tissue, e.g., breast tissue, it can be difficult to properly define the margins of tissue to be removed, both during and after insertion of the needle(s). Also, it is often difficult for the surgeon to detect the exact depth of the lesion based on the placement of the needles. For these reasons it is not uncommon that the biopsied tissue does not contain the mammographically positive specimen. In other cases, as a result of the difficulty of estimating the proper location of the boundaries of the volume of tissue to be removed, the lesion ends up being eccentrically positioned within the volume of tissue excised. This calls into question the adequacy of the margin of normal tissue surrounding the lesion. In still other cases, more normal tissue is removed than is required, which is disadvantageous in this era of tissue-conserving therapies.

Breast lesions are typically excised with a scalpel manipulated directly by the surgeon. With the current emphasis on breast conserving surgical therapies, the above-described procedure for removing a breast lesion is typically performed through a narrow opening in the skin created by slitting and then pulling apart the skin. It tends to be difficult to manipulate the scalpel within this opening so as to remove the desired volume of tissue. The amorphous, pliable nature of breast tissue exacerbates removal of such tissue inasmuch as application of force to the scalpel causes movement of the breast tissue relative to the opening in the skin.

Cryosurgery is a well-established technique used in the treatment of many conditions. Cryosurgery involves the use of a cryoprobe, which is a long, needle-like device that delivers cold to a piece of tissue, thereby destroying the tissue. Cryoprobes typically include an inner tube that delivers a fluid at very cold temperatures, e.g., liquid nitrogen, to an internal orifice positioned near the tip of the cryoprobe. The cold fluid is dispensed through the orifice into a return chamber in the interior of an outer tube surrounding the inner tube. An exemplary cryoprobe is disclosed in U.S. Pat. No. 5,108,390 to Potocky et al., which patent is incorporated herein by reference.

By inserting a cryoprobe into a tissue mass present in a piece of tissue and then activating the cryoprobe, a volume of tissue adjacent to the cryoprobe freezes. The frozen tissue volume can then be removed from the piece of tissue or can be allowed to remain in place for removal by normal bodily function. When freezing a piece of tissue it can be difficult to know when to stop the freezing process so that the frozen tissue volume is of the optimum size. Stopping the freezing process too early will result in the tissue volume being smaller than the tissue mass, with the consequence that all the tissue mass will not be removed. On the other hand, stopping the freezing process too late will result in the tissue volume being substantially larger than the tissue mass, with the consequence that too much healthy tissue will be frozen and removed.

To address this concern, the size of the tissue volume should be monitored during the freezing process. One approach is to monitor the size of the tissue volume using conventional imaging techniques, such as ultrasonic imaging or magnetic resonance imaging (MRI). One example of such approach is described in U.S. Pat. No. 5,531,742 to Barken, ("the '742 patent"), which discloses a surgical system and method of computer controlled cryosurgery that relies on MRI-generated image of the tissue to be frozen. While ultrasound imaging and MRI are, in many cases, reasonably effective techniques for monitoring the freezing of tissue using a cryoprobe, they involve the use of expensive equipment, do not provide adequate guidance as to when a sufficiently large volume of tissue has been frozen and are logistically cumbersome. Also, in some cases effective imaging is impeded by the cryoprobe itself.

Another approach is advocated by ENDOcare Incorporated, of Irvine, California, which markets cryoprobes (e.g., model no. CRYO-40) having a tip capable of measuring temperature. The approach involves inserting a plurality of such cryoprobes or temperature probes into a tissue portion to measure tissue temperature at select locations. However, this technique suffers from the disadvantage that the cryoprobes and temperature probes protrude from the skin above the tissue portion, thus interfering with the surgical removal of the frozen tissue volume. It would, therefore, be greatly advantageous to be able to monitor the growth of a freezing tissue volume in a piece of tissue without the use of devices such as cryoprobes or temperature probes that protrude from the tissue portion and without the use of complex imaging systems.

In animal research studies it is known to obtain animal temperature through the use of a small sensor, also known as a transponder, that is implanted in the animal. Sensors of this type are described in U.S. Pat. Nos. 5,724,030, 5,481,262 and 5,252,962, each to Urbas et al. The sensors described therein provides animal temperature and identification information in an output signal that is received by a receiver system of the type described in U.S. Pat. Nos. 5,420,579, 5,262,772 and 5,250,944, each to Urbas et al. Apparently, a single working sensor is implanted in the animal at any one point in time, and the sensor is used only to obtain animal temperature and identification information. While this system is believed to function effectively for determining a single temperature within a given animal, it is not suitable for assessing a temperature distribution in a portion of human or animal tissue. This is because the system (i.e., sensor and receiver) described in the above-identified patents to Urbas et al. is believed to lack the ability to perform multiple interrogations of different sensors located in close proximity to one another to obtain the temperature data necessary to precisely determine a temperature distribution at the boundary of a relatively small tissue volume. In particular the sensors described in the Urbas et al. patents are not believed to possess the structure and functionality necessary to permit individual sensors to compare an identification code in an interrogation signal provided by the receiver with a unique identification code stored in the sensor and provide temperature information only when the codes match.

SUMMARY OF THE INVENTION

The present invention relates to a method of stabilizing a tissue mass, e.g., a breast tumor or lesion, using temperature sensors, a scanner for determining the temperature of the sensors, and a cryoprobe for freezing and stabilizing the tissue.

One aspect of the present invention is a method of stabilizing and removing a tissue volume having a perimeter. The method comprises the steps of inserting a cryoprobe for freezing tissue in a tissue volume to be stabilized so that a portion of the cryoprobe projects from the tissue volume and freezing the tissue volume with the cryoprobe commencing with regions adjacent the cryoprobe and moving outwardly away from the cryoprobe. In addition, the method includes the steps of monitoring the temperature of the tissue volume adjacent a perimeter thereof during said freezing step and terminating said freezing step when said temperature reaches a first temperature level and removing the tissue volume while grasping the cryoprobe so as to stabilize the tissue volume.

Yet another aspect of the present invention is a method of stabilizing and removing a tissue mass. The method comprises the steps of inserting a portion of a cryoprobe in tissue mass to be removed and freezing the tissue mass with the cryoprobe so that the cryoprobe is attached to the tissue mass. Next, the method involves stabilizing the tissue mass by supporting the cryoprobe in a substantially fixed position and removing the tissue mass.

Other aspects of the present invention are described in the following detailed description of the invention, in the claims and in the accompanying drawings.

BRIEF DESCRIPTION OF THE INVENTION

Figure 1:
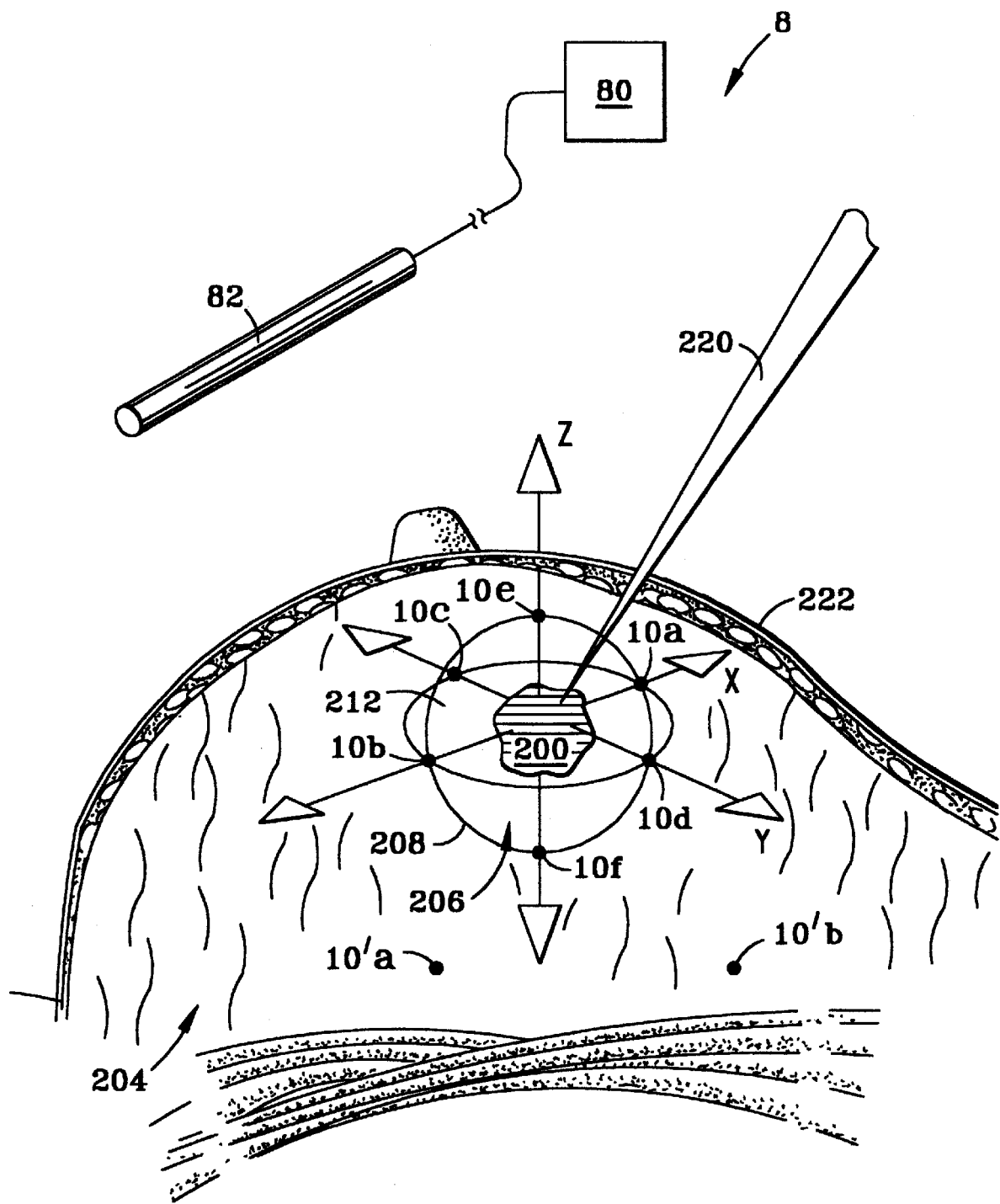
FIG. 1 is a cross-sectional view of a breast containing a tissue mass surrounded by a tissue volume having an outer boundary defined by sensors used in the present invention, with the cryoprobe and detector antenna used in the present invention being illustrated in perspective view.
Figure 10:
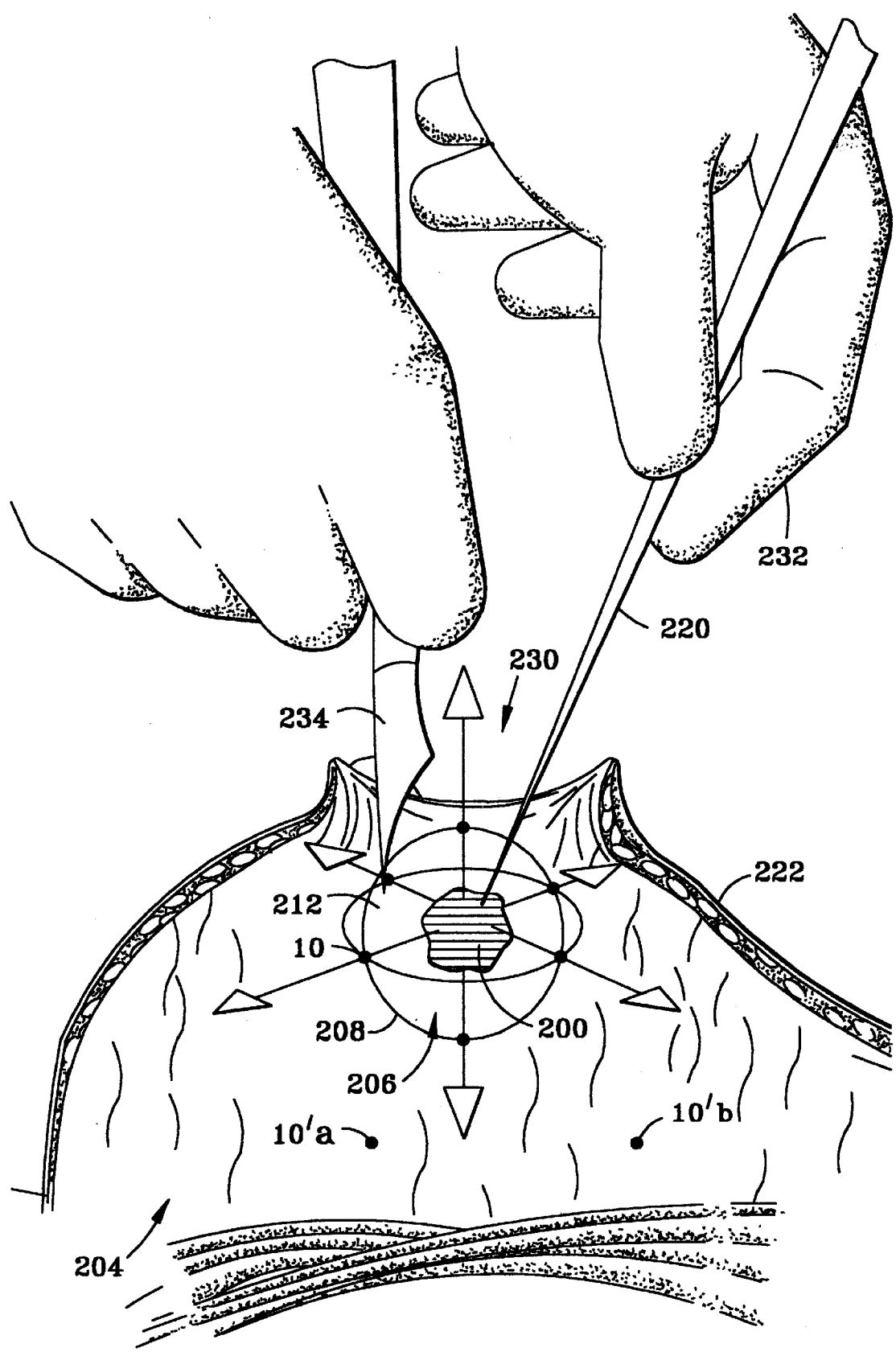
Figure 11:
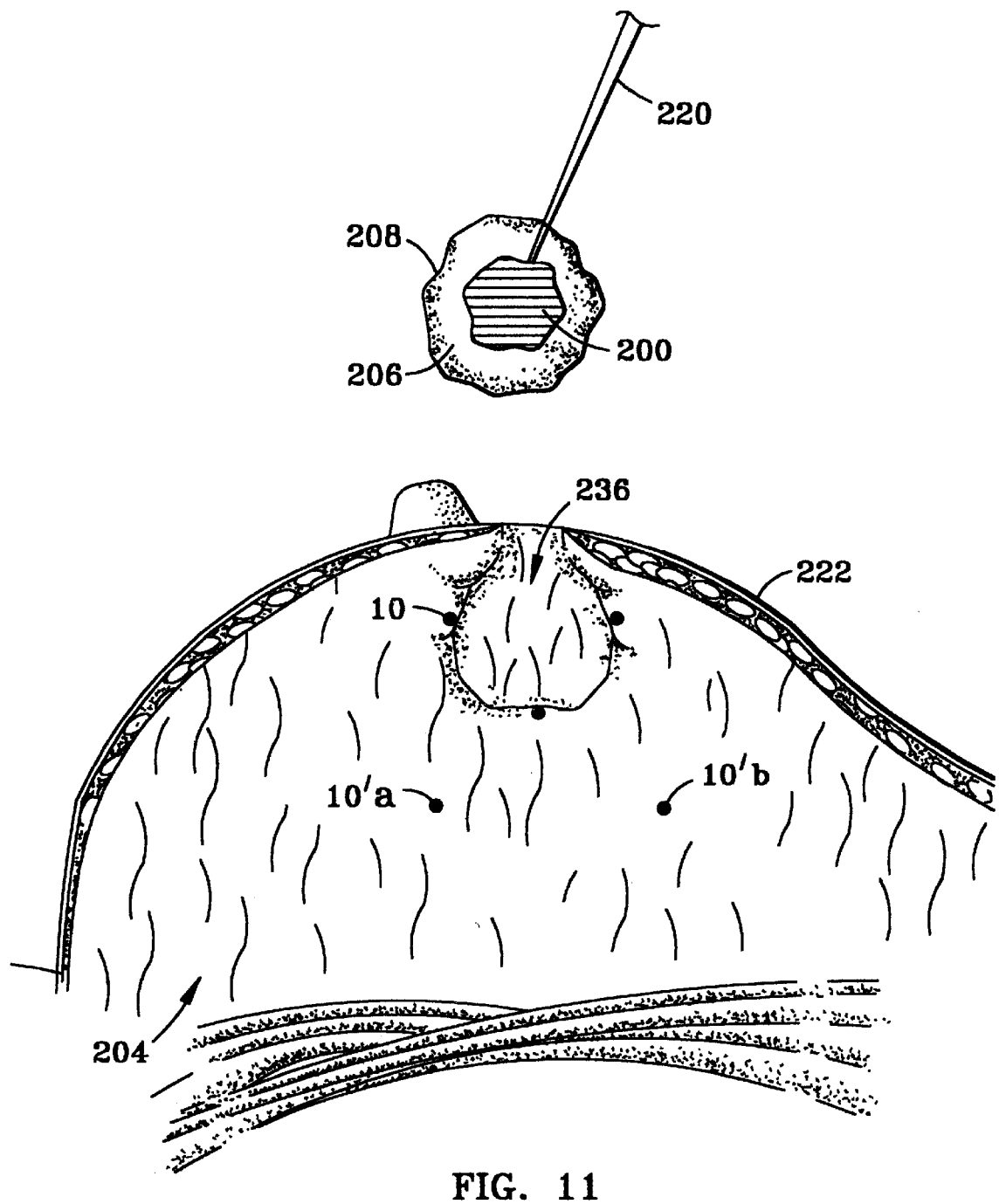

FIG. 10 is the same as FIG. 1, except that an incision has been made in the skin over the tissue volume, the skin adjacent the incision has been pulled apart to provide access to the tissue portion, and a hand is shown grasping the cryoprobe to stabilize the now frozen tissue volume, as a scalpel cuts tissue at the outer boundary of the tissue volume; and FIG. 11 is the same as FIG. 10, but with the frozen tissue volume removed from the breast.

DETAILED DESCRIPTION OF THE INVENTION

Referring to FIG. 1, the present invention relates to a method of stabilizing a tissue mass, e.g., a breast tumor or lesion, using a system 8 that includes temperature sensors 10, a scanner 80 for determining the temperature of the sensors, and a cryoprobe 220 for freezing and stabilizing the tissue. The invention also encompasses a method of stabilizing tissue using cryoprobe 220, without the use of sensors 10 and scanner 80.

Sensor

Figure 2:
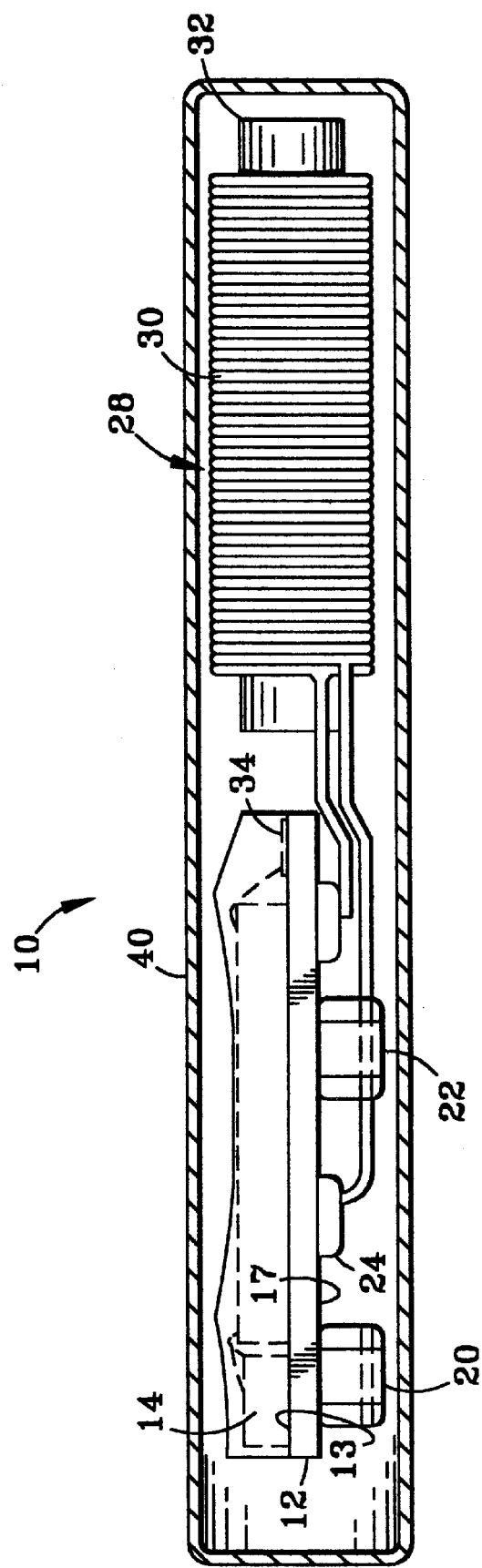
FIG. 2 is a side elevation view of a sensor used in the present invention.

With reference to FIG. 2, the present invention may be practiced using sensor 10 of the type described in aforementioned U.S. Pat. No. 5,724,030 to Urbas et al. ("the '030 patent"), which patent is incorporated herein by reference. Sensor 10 comprises a substrate 12 having an upper surface 13 upon which a temperature measuring unit, such as thermistor 14, is mounted. Also mounted on surface 13 is an electronic assembly 16 having various electronic components such as an EEPROM (not shown), a Manchester encoder (not shown), and a preamble generator (not shown), which are described below with reference to FIGS. 3–5 to the extent not described in the '030 patent. Electronic assembly 16 is preferably, but not necessarily, implemented as an integrated circuit on a single semiconductor chip. Substrate 12 also has a lower surface 17 upon which capacitors 20 and 22 are mounted. Thermistor 14, assembly 16, and capacitors 20 and 22 are electrically connected to each other by metal lines (not shown) disposed on lower surface 17. Sensor 10 includes antenna 28 formed by wrapping a coil 30 around a ferrite rod 32. Coil 30 is coupled to assembly 16 through bonding pads 34. Sensor 10 includes a capsule 40 made from glass or other suitable material that surrounds the aforementioned elements. In a preferred embodiment, capsule 40 has a length in the range 2–15 mm, preferably 3–5 mm, and a diameter (width) in the range 1–5 mm, preferably 2–3 mm.

With reference now to the simplified block diagram of FIG. 3, the sensor described in the '030 patent is modified so that it transmits information when an identification code in an interrogation signal, discussed below, matches the identification code of the sensor. Describing sensor 10 in more detail, assembly 16 further includes a temperature counter 50 connected to receive the output of thermistor 14. Temperature counter 50 is connected so as to provide its output to data encoder/multiplexer 52. The latter is connected to provide its output to data modulator 54. Also included in assembly 16 is a power/data detector 56, which is connected so as to detect an incoming signal received by antenna 28. The output of power/data detector 56 is provided to an ID decoder 58. Assembly 16 further includes memory unit 60 which is also connected to ID decoder 58, and provides sensor identification information to the ID decoder, as described below. Memory unit 60 is a one-time programmable memory, e.g., a semiconductor ROM chip. ID decoder 58 is also connected to data modulator 54, and provides an enabling signal thereto, as described below.

The interconnection and operation of the aforementioned electronic components constituting sensor 10 is now further described. With continuing reference to FIG. 3, antenna 28 receives an interrogation signal from a scanner 80 (not shown in FIG. 3, and discussed below). The interrogation signal contains a sensor identification code, and also provides sufficient power to generate a current for operating sensor 10. The interrogation signal is detected by power/data detector 54, which passes the signal to ID decoder 58. If the ID decoder 58 determines the interrogation signal does not contain the proper sensor identification code, which the ID decoder retrieves from memory 60, then the line XMIT ENABLE ("transmit enabled") connecting ID decoder 58 and data modulator 54 stays low, with the result that no signal is generated by data modulator 54 for transmission by antenna 28.

If ID decoder 58 determines the interrogation signal contains the proper sensor identification code, then the line XMIT ENABLE goes high, thereby enabling data modulator 54 to generate a signal. Meanwhile, current passes through thermistor 14, the resistance of which varies strongly as a known function of temperature. Thermistor 14 provides an analog temperature signal which is converted to a digital temperature signal by temperature counter 50. This temperature signal is then sent to data encoder/multiplexer 52. Data encoder/multiplexer 52 then multiplexes the temperature signal from temperature counter 50 and the sensor identification code from memory 60. This multiplexed signal is then passed to data modulator 54, which creates a radio frequency (RF) signal based on the electronic multiplexed signal inputted thereto. This encoded data signal is then sent out via antenna 28 to scanner 80. By designing sensor 10 to be responsive only to an interrogation signal containing an identification code unique to the sensor, multiple sensors located in close proximity to one another can be used to provide temperature data simultaneously, or nearly simultaneously.

Figure 3:
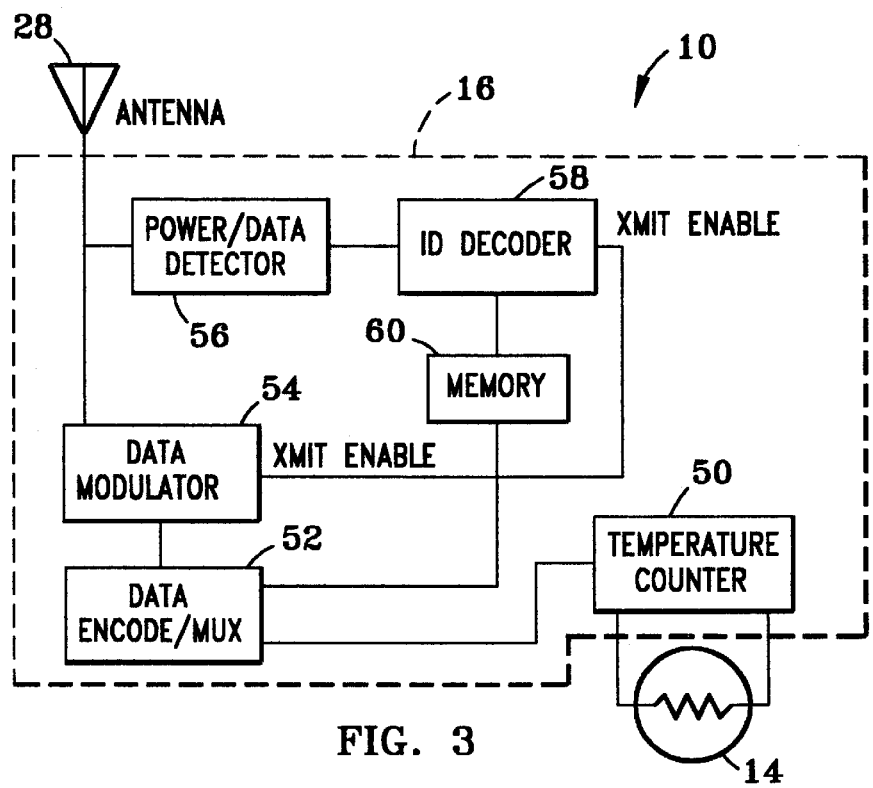
FIG. 3 is a simplified block diagram of a non-programmable sensor used in the present invention.
Figure 4:
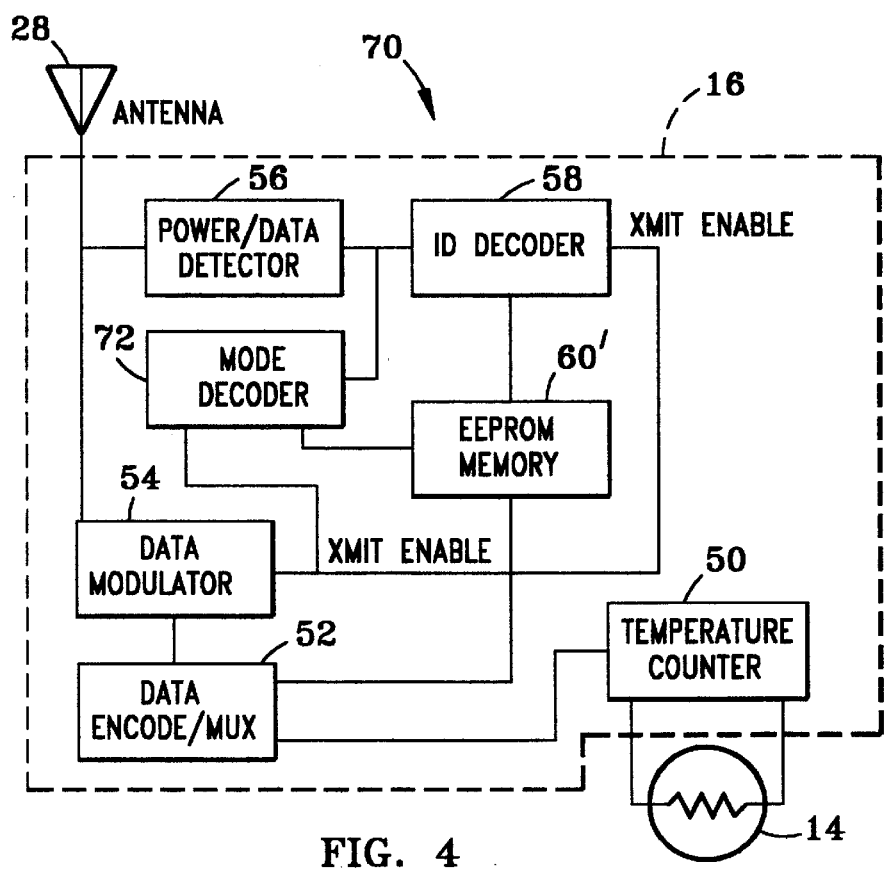
FIG. 4 is a simplified block diagram of a programmable sensor used in the present invention.

Referring now to FIG. 4, there is shown a simplified block diagram of a sensor 70, which is similar to sensor 10 of FIG. 3, except that sensor 70 further includes a reprogrammable memory 60', e.g., an EEPROM chip, in place of memory 60. Memory 60' is connected to mode decoder 72. Mode decoder 72 is also connected to receive the output from power/data detector 56 and is connected to data modulator 54. When an incoming interrogation signal is sensed by power/data detector 56, the latter provides a signal to mode decoder 72 and ID decoder 58 indicative of receipt of such signal. If the received interrogation signal contains code indicating ID programming is to occur (i.e., a sensor ID programming code), mode detector 72 will place sensor 70 in ID programming mode. In this mode, the XMIT ENABLE line connecting ID decoder 58 and data modulator 54 will go high, allowing sensor 70 to handshake with the scanner 80 (not shown). The new sensor ID code is then stored in memory 60'. If the received signal does not contain the proper sensor ID programming code, then ID decoder 58 reads the ID signal from the scanner and compares that sensor ID code to the code stored in memory 60'. If the codes do not match, then the XMIT ENABLE line is left low and no transmission occurs. If the ID codes match, then the XMIT ENABLE line goes high, enabling transmission of the encoded data signal, as described above with respect to sensor 10.

Figure 5A:
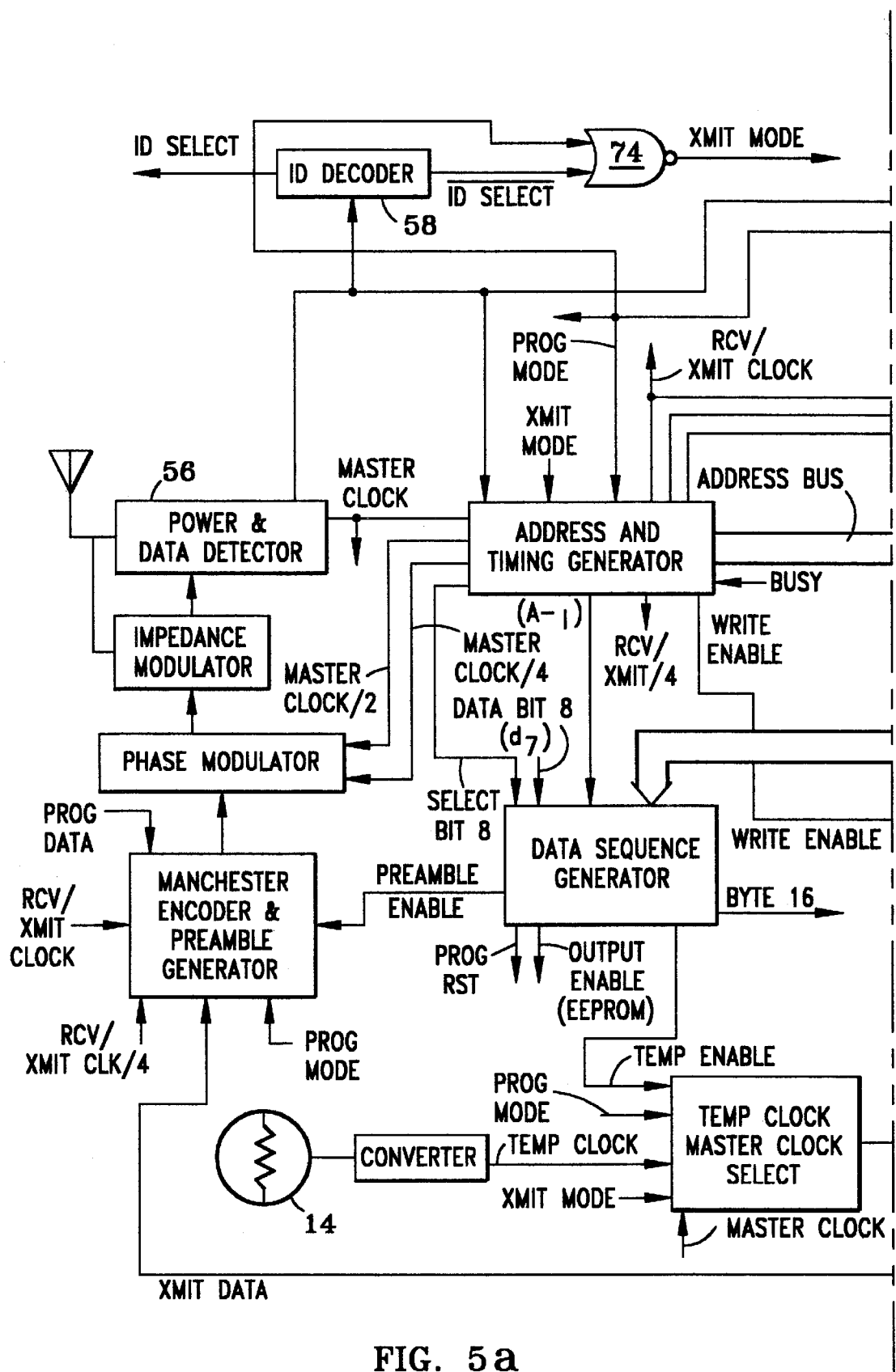
FIG. 5a is a detailed block diagram of a first half of the programmable sensor used in the present invention.
Figure 5B:
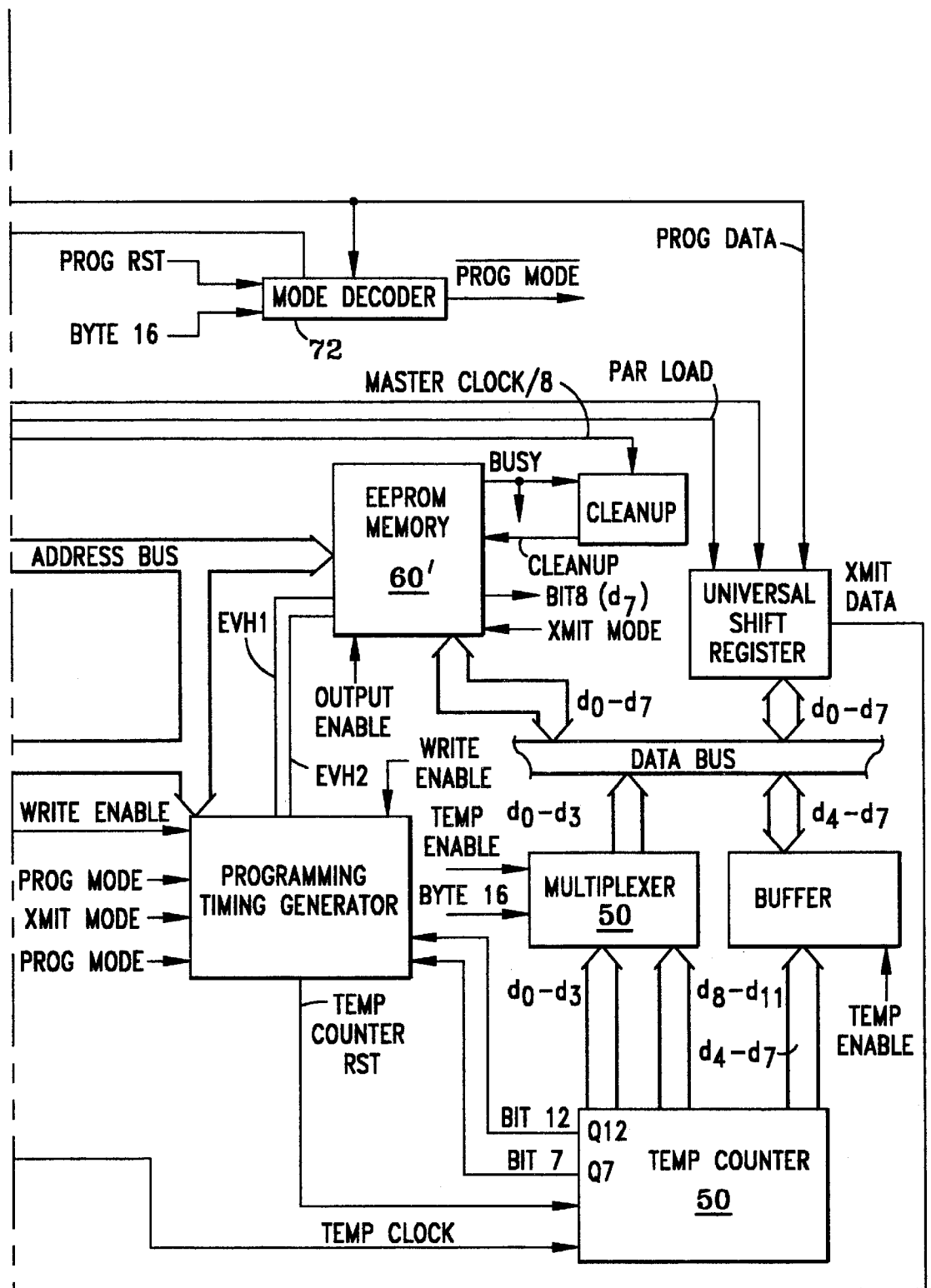
FIG. 5b is a detailed block diagram of a second half of the programmable senor used in the present invention.

With reference now to FIGS. 5a and 5b, sensor 70 is illustrated in more detail. Most of the elements of sensor 70 illustrated in FIGS. 5a and 5b are common to the sensor of the '030 patent, and so are not described herein. Reference should be made to the '030 patent for a description of these elements. Sensor 70 differs from the sensor of the '030 patent in that it includes ID decoder 58 connected to power/data detector 56 and a NOR gate 74 electronically connected to the ID decoder and to mode decoder 72. As described above, ID decoder 58 inhibits the sensor from transmitting unless the ID code transmitted by the scanner matches the pre-programmed code in programmable memory 60'. Transmission is inhibited through the use of NOR gate 74, which provides a transmit enabled signal (high state) to various elements of sensor 70 (adjacent to which are "XMIT MODE" arrows) only when mode decoder 72 is not in programming mode (low state) and ID decoder 58 has determined the proper sensor ID programming code has been received and so is in the low state. The components and functionality of sensor 10 is substantially identical to that of sensor 70 illustrated in FIGS. 5a and 5b and described above, except that memory 60 is used in place of memory 60' and mode decoder 72 and NOR gate 74 are not provided.

Scanner

Figure 6:
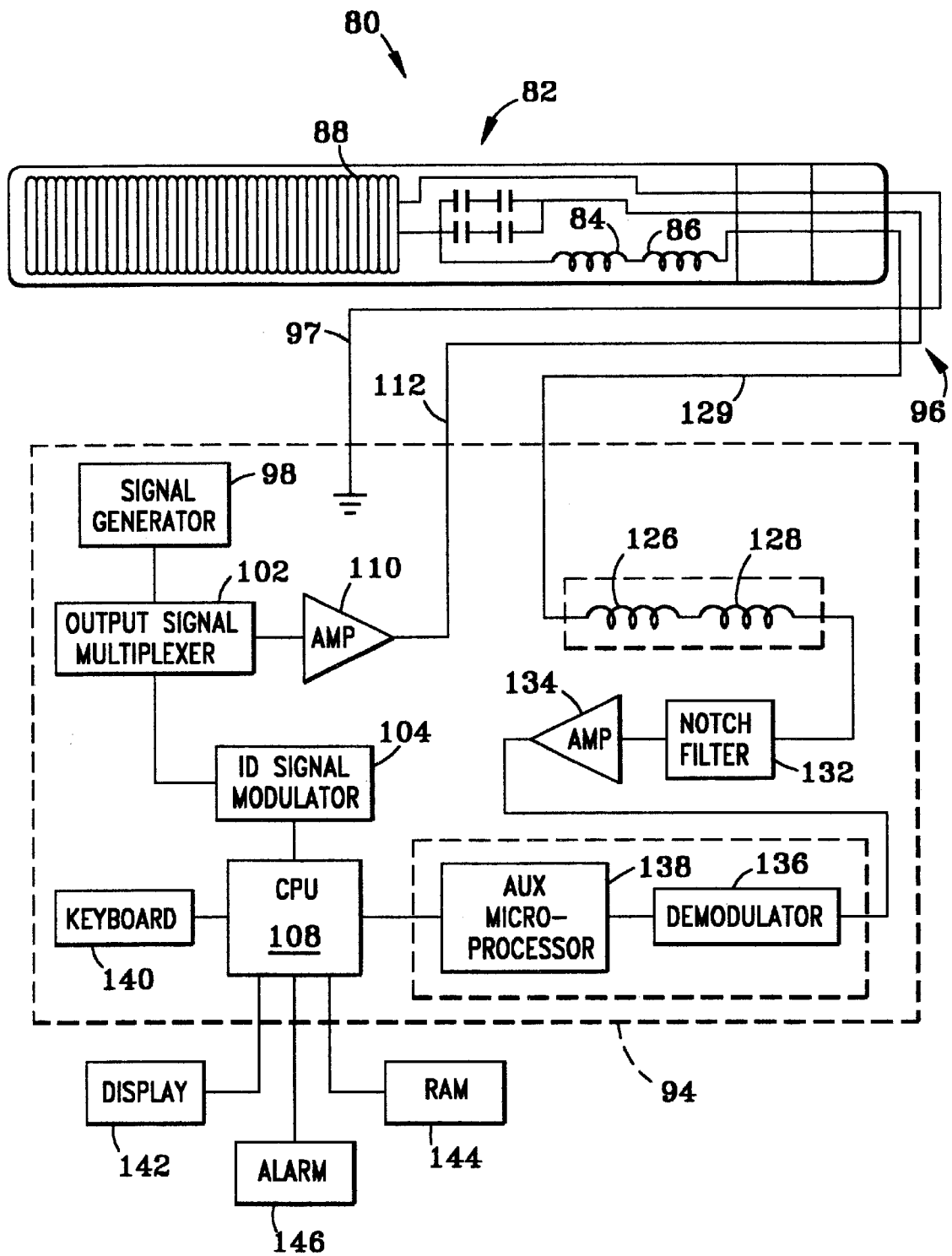
FIG. 6 is a side elevation view of a scanner used in the present invention, including a block diagram of the associated circuitry.

As mentioned above, sensor 10 used the present invention is responsive to scanner 80, which transmits an interrogation signal to, and detects the encoded data signal emitted by, the sensor. With reference now to FIG. 6, scanner 80 of the present invention is similar to the transponder scanner described in aforementioned U.S. Pat. No. 5,262,772 to Urbas et al. ("the '772 patent"), which patent is incorporated herein by reference. Scanner 80 comprises an antenna 82 having a pair of inductors 84 and 86 and an antenna coil 88. Further included in scanner 80 is a microcomputer 94 which is connected via cable 96 to antenna 82. More particularly, antenna 82 is connected to ground via line 97. Microcomputer 94 comprises a signal generator 98 connected to an output signal multiplexer 102, which is connected to an ID signal modulator 104 and an amplifier 110. The output of amplifier 110 is provided via line 112 in cable 96 to antenna 82. ID signal modulator 104 is also connected to CPU 108.

Also included in microcomputer 94 is a pair of inductors 126 and 128 connected to receive a signal from antenna 82 via line 129. A notch filter 132 is connected to receive the signal from inductors 126 and 128, and deliver the signal to amplifier 134. Amplifier 134 amplifies the signal from inductors 128 and 128 and transmits it to demodulator 136. The output of demodulator 136 is provided to auxiliary microprocessor 138, the output of which is provided to CPU 108. Auxiliary microprocessor 138 provides a machine-usable signal to CPU 108, as described below. Also connected to CPU 108 are keyboard 140, display 142, RAM 144 and alarm 146. Display 142 may be a computer monitor, a series of LEDs, an LCD display or other means for displaying temperature information for sensors 10. Preferably display 142 is constructed so that temperature information is displayed for each sensor 10. Temperature information may be displayed in degree units or in a relative sense by, for example, a bar graph that increases in length with decreases in temperature. RAM 144 preferably comprises semiconductor random access memory. Alarm 146 may be a speaker or tone generator for creating a sound, a flashing light or other means for attracting attention.

Referring to FIGS. 2 and 6, the interconnection and operation of the aforementioned electronic components constituting scanner 80 is further discussed. Signal generator 98 generates an RF reference signal of, for example, 400 KHz. RAM 144 stores the different sensor identification codes, and sends a signal containing one of the identification codes to modulator 104. Modulator 104 then modulates the signal so as to create an RF signal containing the sensor identification code and passes the modulated signal along to output signal multiplexer 102. Multiplexer 102 then multiplexes the encoded modulated signal from modulator 104 and the signal from signal generator 98. This multiplexed signal is then amplified by amplifier 110 and is sent to antenna 82 along a line 112 in cable 96 connected to the antenna. The multiplexed signal is then transmitted via antenna 82 as an RF interrogation signal. This signal is then detected by antenna 28 in sensor 10 (see FIG. 2).

Scanner 80 also receives an RF encoded data signal generated by sensor 10 in response to the interrogation signal. The encoded data signal from sensor 10 includes temperature data and the sensor identification code of the particular sensor. This encoded data signal is detected by antenna 82 and then is passed through inductors 84 and 86 in the antenna, which act as a low band-pass filter. The filtered signal is then passed to microcomputer 94 along line 129 contained within cable 96. This filtered signal then passes through inductors 126 and 128, which act as a second low band-pass filter for filtering out high-frequency signal on the line. This twice-filtered signal is then passed through notch filter 132 to filter background noise, and is then amplified by amplifier 134. The amplified signal is then provided to demodulator 136, which senses the encoded signal and, in conjunction with an auxiliary microprocessor 138, translates the encoded signal into a machine-usable signal. This signal is then transmitted to CPU 108. CPU 108 then manipulates the temperature and sensor identification code data contained within the machine-usable signal in accordance with input from keyboard 140. The data may also be displayed on display 142 in any one of a variety of humanly recognizable representations, or stored in RAM 144. In addition, CPU 108 may send a signal to alarm 146 when the temperature of the sensor 10 exceeds a set temperature threshold, as discussed below.

Sensor 70 functions with scanner 80 in the same manner as sensor 10, discussed above. As such, a detailed description of this operational relationship is omitted.

Figure 7:
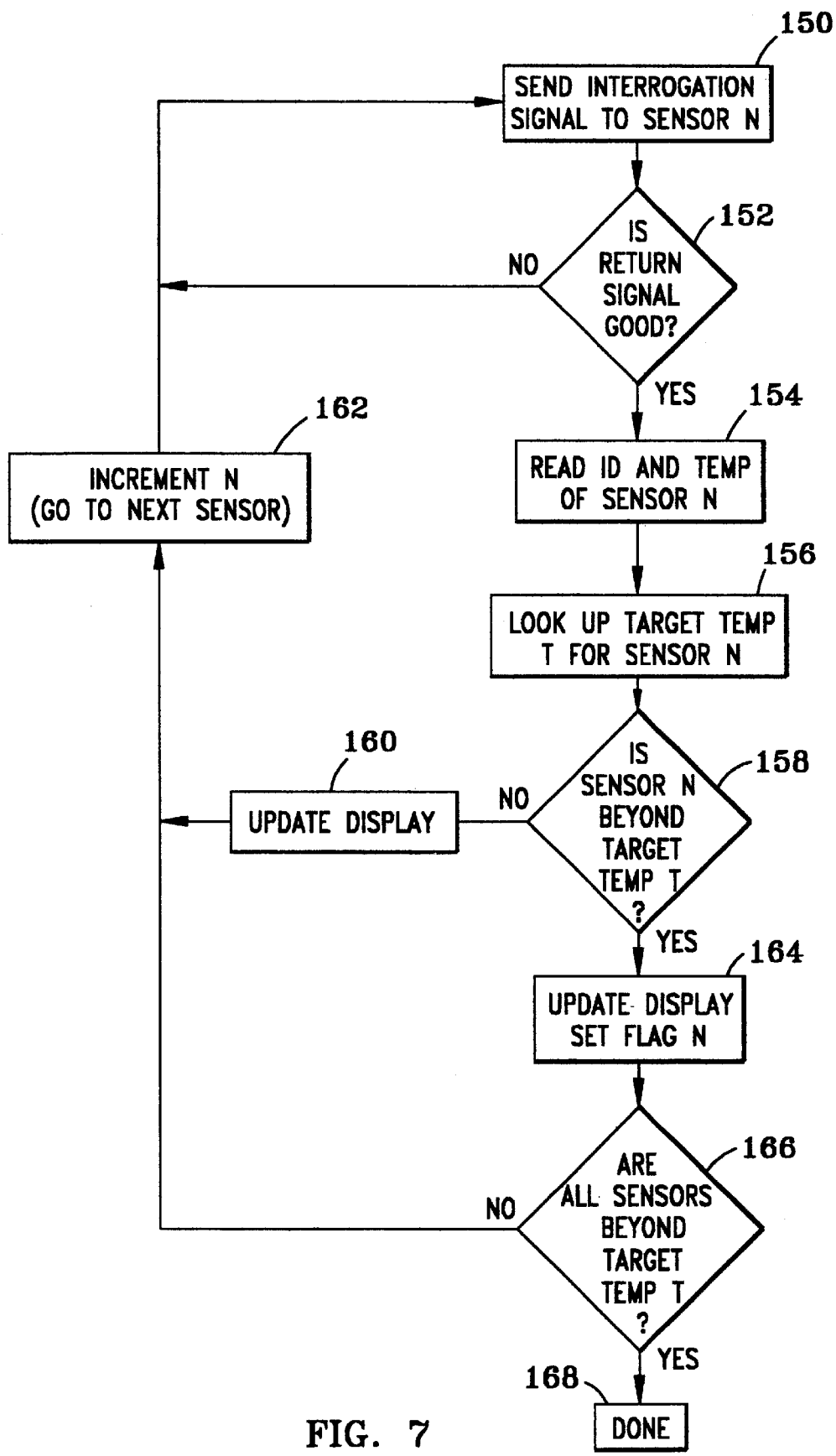
FIG. 7 is a flow diagram of the steps of one embodiment of the present method of sensing temperature using the plurality of sensors and scanner used in the present invention.

Referring to FIGS. 1–7, in the present invention, a plurality of sensors 10 or 70 (i.e., N sensors, N>1) located in close proximity to one another are preferably used to determine the temperature distribution in a given tissue volume 206 within which cryoprobe 220 is inserted, as described in more detail below. (For convenience, unless otherwise indicated, sensors 10 and 70 are collectively referred to hereinafter as sensor 10.) This is achieved by positioning sensors 10 within the tissue volume 206 and obtaining temperature information from each sensor, as is described further below. To achieve this functionality, microcomputer 94 is programmed in a way not described or contemplated in the '772 patent so as to successively interrogate sensors 10 to assess the temperature of tissue immediately adjacent the sensor. This programming is illustrated in FIG. 7 and described below.

As the first step in the routine for interrogating sensors 10, indicated by step 150 in FIG. 7, scanner 80 sends an interrogation signal to the $N^{th}$ sensor 10. Next at step 152, an assessment is made whether the return encoded data signal from the $N^{th}$ sensor 10 is "good," i.e., readable by scanner 80. If it is not, then the routine returns to step 150 and another interrogation signal is sent to the $N^{th}$ sensor 10. If the encoded data signal is "good," then at step 154 the identification code and the temperature data in the encoded data signal are read (i.e., decoded) from the $N^{th}$ sensor 10. Then, at step 156, the target temperature T, stored in RAM 144, for the $N^{th}$ sensor 10 is looked up by CPU 108. At step 158, an assessment is made as to whether the temperature reading provided by the $N^{th}$ sensor 10 is beyond (i.e., below) the target temperature T. If it is not, at step 160, display 142 is updated with an indication of the temperature read by sensor 10. As noted above, temperature may be indicated by illuminating an electronic bar graph, digitally displaying the temperature or otherwise depicting the temperature in a humanly readable form. Then, as indicated by step 162, the above steps are repeated for the next (i.e., N+1) sensor 10.

With continuing reference to FIG. 7, returning to step 158, if the temperature of the $N^{th}$ sensor 10 is beyond the target temperature T, then at step 164, display 142 is updated and a flag is set for this $N^{th}$ sensor 10 indicating the sensor temperature reading is beyond target temperature T. Display 142 is updated in the manner discussed above. Next, at step 166, a determination is made whether all the sensors 10 are beyond the target temperature T by referring to the status of the flags for all the sensors. If not, then the routine is to return to step 162 and repeats the above steps 150–164 for the next (i.e., N+1) sensor 10. On the other hand, if all the sensors 10 are beyond the target temperature, then the routine is done, as indicated by step 168.

With reference now to FIGS. 1, 2, 6 and 8, another preferred embodiment for determining a temperature distribution using sensors 10 and scanner 80 of the present invention is now described. The flow diagram of FIG. 8 includes all steps in the flow diagram of FIG. 7, described above, and further includes the additional step 172, after step 158, of assessing whether the $N^{th}$ sensor 10 is beyond a predetermined "safe" temperature S. If not, then the routine proceeds to step 164, as described above. However, if the temperature of the $N^{th}$ sensor 10 is beyond safe temperature S, then the routine proceeds to the next step 174, where alarm 146 is activated for the $N^{th}$ sensor 10 to alert a human observer/operator. Based on this alert, the observer/operator assesses if cryoprobe 220 should continue to be used to freeze tissue volume 206. The routine then continues to step 164 and proceeds as discussed above in connection with FIG. 7.

Selection of an appropriate target temperature T and safe temperature S for sensors 10 is an important aspect of the setup programming of scanner 90. These temperature values may be the same, but to achieve the full benefits of the routine illustrated in FIG. 8 and described above, safe temperature S is typically lower than target temperature T. In addition, target temperature T and safe temperature S may be the same for all sensors 10, the same for given categories of sensors 10 or different for each sensor 10.

For sensors 10 that are positioned to define tissue volume 206, i.e., lie on perimeter 208, target temperature T is in most cases 0° C. However, depending on tissue composition, the quantity of cooling delivered by cryoprobe 220 and other factors, it may be desirable to select target temperatures T for such sensors 10 above or below 0° C. More particularly, the tissue volume 206 may, in some instances, continue expanding outwardly after the delivery of cold (more precisely, the removal of heat) by cryoprobe 220 is terminated. Therefore, the target temperature T may, in these instances, be set to a higher temperature, such as 5° C., to account for continued expansion of the frozen tissue volume.

For sensors 10 that are positioned to define tissue volume 206, safe temperature S is typically about 5–10° C. lower than target temperature T. However, other temperature relationships between safe temperature S and target temperature T are encompassed by the present invention.

An important aspect of the present invention, as described in more detail below, is achieved by implanting sensors 10' in tissue portion 204 so as to lie well outside tissue volume 206. Two such sensors, sensors 10'$a$ and 10'$b$ are illustrated in FIG. 1. Target temperature T for sensors 10' is typically set at normal body temperature. Safe temperature S is less than target temperature T an amount that varies as a function of the placement of a given sensor 10' relative to perimeter 208 of tissue volume 206, the type of other tissue adjacent the tissue volume, surgeon preference and other factors. As such, safe temperature S may be just few degrees lower than target temperature T, may be significantly lower than target temperature T, e.g., 0° C., or may be an intermediate amount, e.g., 20–35° C., lower than target temperature T. As with sensors 10, target temperature T and safe temperature S may be the same for all sensors 10', may be different for each sensor 10', or may the same for some but not all of sensors 10'.

Cryoprobe

Referring again to FIG. 1, system 8 used in the present invention includes cryoprobe 220. The latter includes a tip, which is not visible in FIG. 1 because it is inserted in tissue mass 200, for delivering cold to the tissue mass. Cryoprobe 220 is a conventional cryoprobe of the type disclosed in U.S. Pat. No. 5,108,390 to Potocky et al. ("the '390 patent") which, as noted above, is incorporated herein by reference. For more details concerning the construction of cryoprobe 220, attention is directed to the '390 patent. Another cryoprobe that may be satisfactorily employed as cryoprobe 220 is manufactured by ENDOcare Incorporated of Irvine, Calif., and identified by part numbers CRYO-24, CRYO-22 and CRYO-20. Cryoprobe 220 is connected to a first source of fluid (not shown), e.g., liquid nitrogen, to cool the tip of cryoprobe 220 and is preferably, but not necessarily, connected to a second source of fluid to heat the tip of the cryoprobe.

Defining The Tissue Volume To Be Frozen

Referring now to FIG. 9$a$, an important aspect of the present invention is the use of the above-described sensor 10 (which reference number continues to be used generically to refer to sensors 10 or 70) and scanner 80 of the present invention as part of a system 8 for and method of stabilizing and removing a tissue mass 200, such as a breast tumor, from a larger portion of tissue 204. In the present invention, a tissue volume 206 surrounding the tissue mass 200 is defined, and is then frozen with cryoprobe 220. Instead of partially thawing a portion of tissue mass 200 and removing cryoprobe 220, in the present invention the cryoprobe typically remains frozen to the tissue mass. The cryoprobe is then used as a handle to stabilize tissue volume 206 during its subsequent removal.

In one embodiment of the method of the present invention, a plurality of sensors 10 are arranged about a tissue mass 200, e.g., a breast lesion, in a tissue portion 204. Tissue portion 204 may be a part of any organ or structure, e.g., a breast or liver, or may constitute an entire organ or structure. The initial location of tissue mass 200 is determined through conventional imaging methods, e.g., ultrasound, MRI, X-ray or CAT scan. Next, sensors 10, such as sensors 10$a$–10$f$, are implanted in tissue portion 204 surrounding tissue mass 200, thereby defining an outer perimeter 208 of a tissue volume 206. The number of sensors 10 used, and the placement of the sensors relative to tissue mass 200, will vary depending upon the desired size of the tissue volume 206 to be frozen, the location of the tissue mass relative to other types of tissue, e.g., bone or muscle, surgeon preference, and size and configuration of the tissue mass. However, in many applications, it will be desirable to use at least six sensors 10 to surround tissue mass 200, preferably two on each of mutually orthogonal axes X, Y and Z, on opposing sides of tissue volume 206, as shown.

While it is preferred that axes X, Y and Z be mutually orthogonal and intersect tissue mass 200, as illustrated, this is not mandatory and can be difficult to precisely implement in practice. However, it is generally preferable that tissue mass be completely surrounded by sensors 10. Also, while the X, Y and Z axes are illustrated in FIG. 9$a$ as intersecting at a common point centrally located within tissue mass 200 this is not required. For example, it may be desirable to offset the X and Y axes somewhat, as measured along the Z axis. Furthermore, while tissue volume 206, as illustrated in FIG. 9$a$, has a spherical configuration, it is to be appreciated that the configuration of tissue mass 200 dictates the configuration of the tissue volume. For example, if tissue mass 200 has an oval configuration, then sensors 10 are preferably positioned so that tissue volume 206 has a corresponding, although larger, oval configuration.

In some cases, it will be desirable to use more than two sensors 10 on X, Y and Z axes. In other cases, it will be desirable to use fewer sensors. For example, with reference to FIG. 9$b$, it may be desirable to locate sensors along only two axes, thereby defining a perimeter 208' of a planar tissue area 206'. The actual number and relative placement of sensors 10 will vary according to the situation, and the various arrangements will be apparent to one skilled in the art and are encompassed by the present invention.

With reference once more to FIG. 9$a$, sensors 10 are preferably spaced from tissue mass 200 so as to define a tissue margin 212 (i.e., that portion of tissue volume 206 between perimeter 208 and tissue mass 200) large enough to ensure none of tissue mass 200 lies outside tissue volume 206. The precise size of tissue margin 212 will vary with the nature of the tissue mass 200, the size of the tissue mass, surgeon preference and other factors. However, tissue margin 212, as measured outwardly along an axis extending perpendicular to a surface location on tissue mass 200, is generally about 0.5–3 cm, and is preferably about 1.0 cm.

With continuing reference to FIG. 9$a$, sensors 10 may be implanted in tissue portion 200 in a variety of different ways using a variety of different tools. In general, sensors 10 are implanted using a conventional imaging system (not shown) that simultaneously generates an image of tissue mass 200 and the sensors. By frequently comparing the location of sensors 10 to tissue mass 200 during implantation of the sensors into tissue portion 204, based on image information received from the imaging system, the sensors may be positioned so as to define tissue volume 206 in the manner described above.

It is preferable to at least partially immobilize tissue portion 24 during implantation of sensors 10. However, this is less critical than might be expected because by comparing the relative location of a sensor 10 to tissue mass 200, the desired relative placement can typically be achieved, even if tissue portion 204 is moving during marker implantation.

Figure 8:
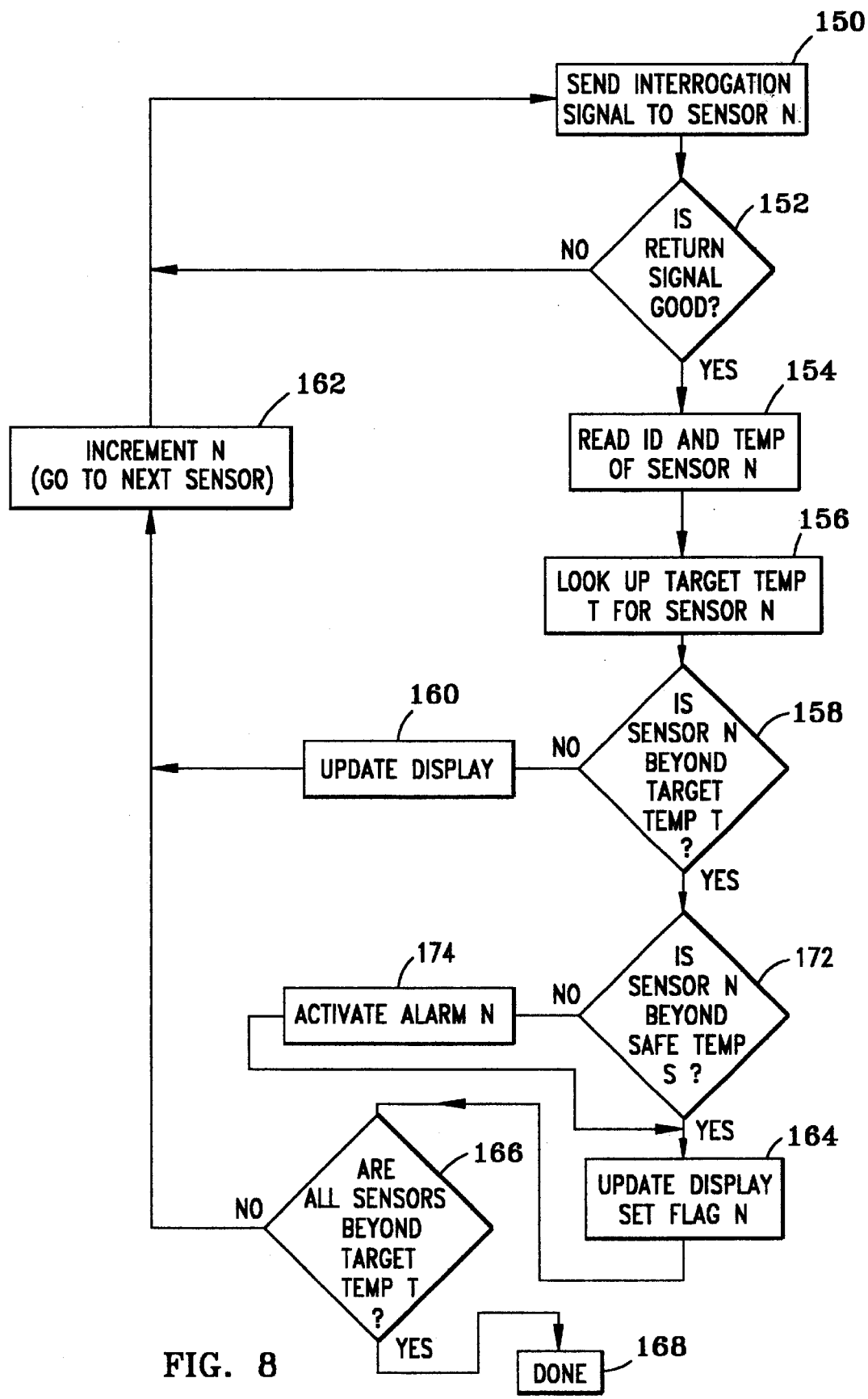
FIG. 8 is a flow diagram of the steps of a second embodiment of the present method of sensing temperature using the plurality of sensors and scanner used in the present invention.
Figure 9A:
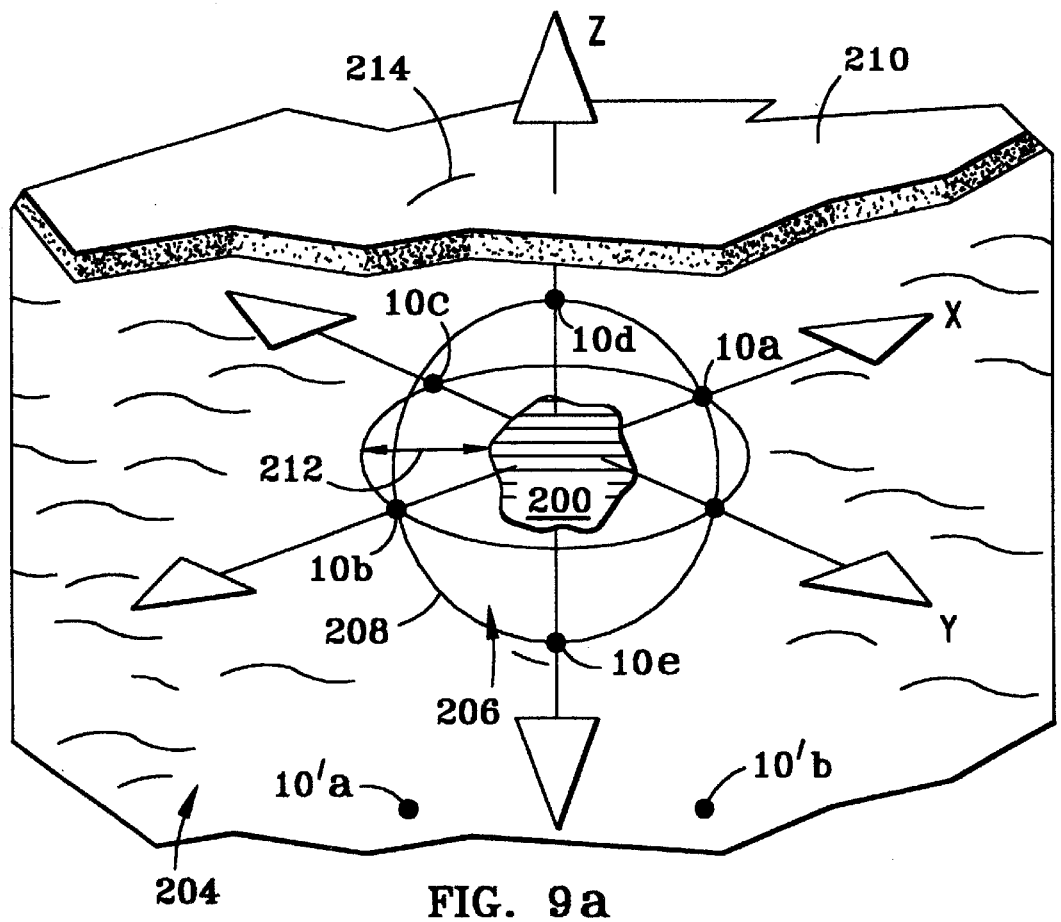
FIG. 9a is a perspective view of a tissue portion within which is contained a tissue mass surrounded by a three-dimensional tissue volume having an outer boundary defined by sensors disposed on either size of the tissue mass along mutually orthogonal X-Y-Z axes that intersect the tissue mass.
Figure 9B:
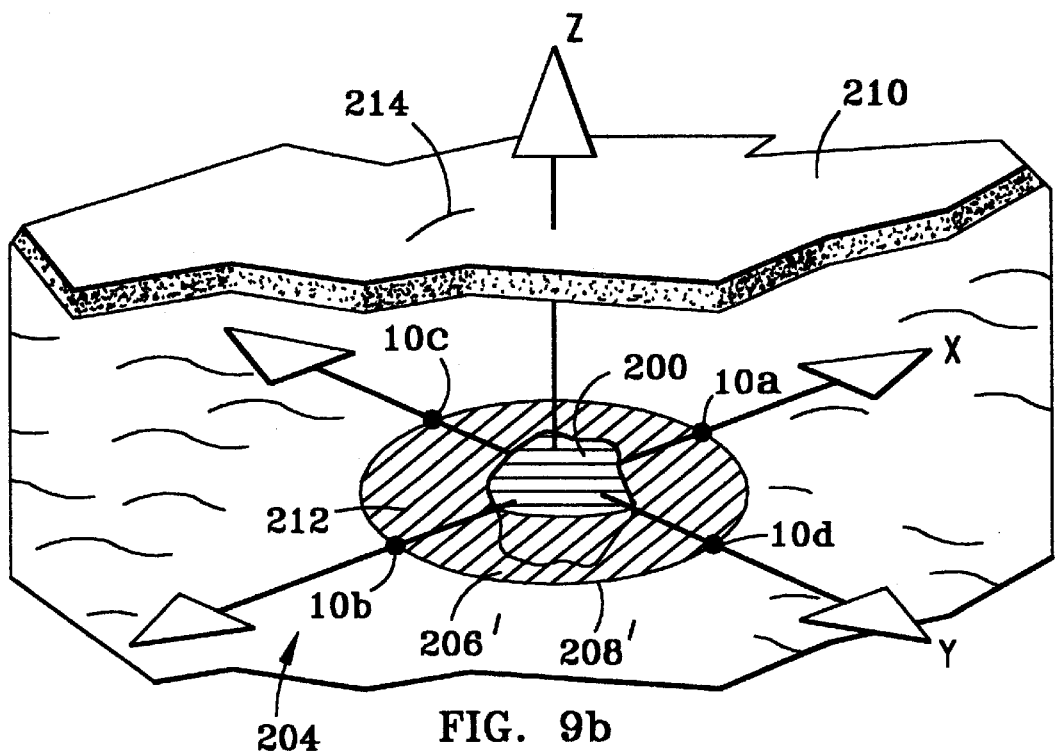
FIG. 9b is a perspective view of a tissue portion containing a tissue mass surrounded by a two-dimensional tissue volume having an outer boundary defined by sensors disposed on either size of the tissue mass along mutually orthogonal X-Y axes that intersect the tissue mass.

With continuing reference to FIG. 9a, in addition to sensors 10a–10f, additional outlying sensors 10'a and 10'b, are optionally, but preferably, disposed in tissue portion 204 outside tissue volume 206, as shown. As discussed above in connection with FIGS. 7 and 8, such outlying sensors 10'a and 10'b can be used to add an extra margin of safety, by providing temperature readings that can be used to prevent regions of tissue portion 204 or other organs adjacent tissue volume 206 from being subjected to extreme temperatures. While two outlaying sensors 10' are illustrated in FIG. 9a, the present invention encompasses the use of one or more than two sensors 10'.

Sensor Implantation

Various techniques may be used to implant sensors 10 in tissue portion 204. With continuing reference to FIG. 9a, one approach is to insert sensors 10 percutaneously through skin 210 overlying tissue portion 204, using known needle pushers or implanters (neither shown) of the type used to implant "seeds" of radioactive material for various cancer treatments. For example, needle pushers of the type sold by Best Industries of Springfield, Va., may be satisfactorily employed. These needle pushers include a central needle surrounded by an outer tube having an end plate or cup for supporting the radioactive "seed." Following insertion of the needle pusher into the selected tissue mass, the radioactive "seed" (which, in the present invention, is a sensor 10) is released by pressing the central needle downwardly relative to the surrounding outer tube, with the point of the needle ejecting the "seed" sensor from the end plate or cup of the outer tube.

To percutaneously insert sensor 10 in accordance with this first approach, the sensor is positioned on the end of the needle pusher, is forced through skin 210 and, using feedback from the imaging system, is guided to the region where it is desired to implant the sensor. Then sensor 10 is ejected from the needle pusher by urging the central needle forward.

A second approach for implanting sensors 10 involves creating a small, e.g., 5–10 mm, incision 214 in skin 210 overlying tissue portion 204. Next, a scalpel (not shown) is inserted through incision 214 so as to form a slit (not shown) in the underlying tissue portion extending to the position where it is desired to implant a sensor 10. Then a sensor 10 is inserted through the slit to such position using a tweezers, needle pusher, trocar or other tool to hold the sensor. Other sensors 10 are implanted through separate incisions in skin 210 in similar manner so as to define a tissue volume 206.

With continuing reference to FIG. 9a, a third approach for implanting sensors 10 is to form a relative large, e.g., 1–3 cm, incision (not shown) in skin 210 overlying tissue mass 200. Next, the incision is pulled open using retractors (not illustrated) or other conventional devices so as to form a relatively large open region above tissue mass 200. Sensors 10 are then implanted into tissue portion 204 via the open region using either of the first or second approaches described above.

Other approaches for implanting sensors 10 so as to surround tissue mass 200 are also encompassed by the present invention. The speed and accuracy with which sensors 10 may be implanted, and minimizing trauma associated with implantation, are important objectives to consider in selecting other approaches for implanting the sensors.

Stabilizing and Removing Tissue

Referring now to FIG. 1, system 8 may be used in connection with various embodiments of the method of the present invention for stabilizing and removing tissue. As the first step in a each of these embodiments, cryoprobe 220 is inserted into tissue mass 200, e.g., in breast 222, which has been previously identified using conventional imaging technology, e.g., MRI or ultrasound. As also discussed above, tissue volume 206 has been defined by inserting sensors 10 in tissue portion 204 so as to surround tissue mass 200 and define the tissue volume. Insertion of cryoprobe 220 is typically achieved by comparing the location of the cryoprobe with the location of tissue mass 200, as identified with the imaging system employed. Cryoprobe 220 is preferably inserted so that its tip is substantially centered within tissue mass 200. However, in certain circumstances it may be desirable to insert cryoprobe other than at a centered location with respect to tissue mass 200.

With reference now to FIGS. 1–4, 5a and 5b, 6–8 and 9a and 9b, scanner 80 is operated so as to obtain and display the temperature information generated by each sensor 10 surrounding tissue volume 206 on a sequential and repeated basis. This is achieved in accordance with the routines described above and illustrated in FIGS. 7–8, which routines are only briefly referenced in connection with the following description of the present method of stabilizing and removing tissue.

As the first step in such method, cryoprobe 220 is activated to freeze tissue mass 200. At the next step scanner 80 is operated to generate an interrogation signal encoded with the identification code of one of sensors 10a–10f (see step 150, FIGS. 7–8). In this description the number of sensors 10 used is for purposes of explanation, not as a limitation on the method. Each of the sensors 10a–10f compares the identification code in the interrogation signal with its own unique identification code stored in memory 60 to assess if a match exists. The one sensor of sensors 10a–10f having the matched identification code then emits an encoded data signal, which contains sensor identification information and temperature information corresponding to the temperature adjacent the sensor. Display 142 of scanner 80 is updated with the temperature information for the one sensor 10, and the process is repeated for the next sensor 10. When all the sensors 10 have been interrogated and their temperature data recovered and displayed, the process is repeated.

As time goes by, cryoprobe 220 causes tissue mass 200 to grow continuously colder and eventually freeze. This freezing continues radially outwardly from cryoprobe 220, and the corresponding change in temperature is detected by sensors 10a–10f. The freezing process is continued until the temperature of each sensor is below the target temperature T (see FIGS. 7–8, step 166).

With reference to FIGS. 1 and 8, in another embodiment of the present method of stabilizing and removing tissue, scanner 80 also indicates whether the temperature of each sensor 10 is beyond a preset safe temperature S (see FIG. 8, step 172), as described above. If so, scanner 80 activates its alarm 146 so as to warn an observer/operator.

With reference to FIGS. 1, 7 and 8, in another preferred embodiment, additional sensors 10'a and 10'b, located in tissue portion 204 outlying tissue volume 206, are used. As described above in connection with the flow diagrams in FIGS. 7 and 8, sensors 10'a and 10 'b are interrogated by scanner 80 and provide temperature data in the outlying tissue portion 204, to ensure that the frozen tissue volume 206 remains localized and does not extend into adjacent tissue that would be damaged by freezing. In the event the temperature data provided by sensors 10'a and 10'b indicate the temperature in tissue portion 204 outlying tissue volume 206 has gone below the "safe" temperature T, then alarm 146 is activated, thereby providing an operator with the chance to halt delivery of cold by cryoprobe 220. As those skilled in the art will appreciate, selection of a safe temperature T depends upon the composition of tissue portion 204 and adjacent tissue to be protected, the distance between perimeter 208 of tissue volume 206 and sensors 10'a and 10'b, and the nature of tissue mass 200.

Because cryoprobe 220 is inserted into tissue mass 200, it typically becomes frozen to, and thus fixedly attached within, tissue volume 206. This is advantageous because as mentioned cryoprobe 220 can be grasped like a handle so as to stabilize tissue volume 206. This greatly facilitates the removal of tissue volume 206, as described below.

With reference now to FIG. 10, tissue volume 206 is removed by first forming an opening 230 in breast 222 to access now frozen tissue volume 206. The surgeon or other person assisting with the procedure holds cryoprobe 220 with their hand 232 to stabilize tissue volume 206. Because tissue volume 206 is anchored to the tip of cryoprobe 220 by virtue of it being frozen to the tip, the surgeon can readily determine the location and configuration of the tissue volume. Then, in a preferred embodiment of the present invention, a scalpel 234 is used to cut around perimeter 208 of tissue volume 206, until the tissue volume is free from tissue portion 204. Alternatively, tissue volume 206, upon freezing, may be sufficiently loosely connected to surrounding tissue portion 204 than it can be removed from tissue portion 204 simply by gently pulling upward on cryoprobe 220, or by first cutting away a small amount of tissue connecting tissue volume 206 to tissue portion 204. This removal of tissue volume 206 is greatly facilitated by virtue of the fact that the tissue volume is stabilized by cryoprobe 220.

It is generally preferred that cryoprobe 220 be held in the hand 232 of the surgeon or assistant because of the tactile feedback achieved with this approach. However, the present invention encompasses methods in which cryoprobe 220 is supported in a substantially fixed position relative to tissue volume 206 using a stereotactic device, gantry or other known devices for securing an implement in a substantially fixed position.

With reference now to FIGS. 10 and 11, using either of the above-described removal methods, the surgeon or assistant then removes cryoprobe 220 with tissue volume 206 and tissue mass 200 attached thereto, leaving a tissue cavity 236 substantially the size of tissue volume 206.

In yet another embodiment of the present method of stabilizing and removing a tissue mass, the expanding size of the tissue volume 206 as it is frozen is monitored by conventional methods of biomedical imaging, such as MRI or ultrasound, rather than with system 8. With this embodiment, cryoprobe 220 is inserted into tissue mass 200 using conventional biomedical imaging, as discussed above in connection with the embodiment in which system 8 is used in performing the method. Next, cooling fluid is delivered to the tip of cryoprobe 220 so as to cause tissue mass 200 and adjacent portions of tissue volume 206 to freeze, commencing adjacent the tip and moving radially outwardly. This freezing of tissue volume 206 is concurrently monitored by imaging tissue portion 204 with conventional biomedical imaging systems. Once tissue volume 206 is entirely frozen, the delivery of cooling fluid to the tip of cryoprobe 220 is terminated.

The physician operating cryoprobe 220 to freeze tissue volume 206 determines when the tissue volume has acquired the desired size, i.e., when tissue margin 212 is sufficiently large, by comparing the boundaries of tissue mass 200 displayed by the imaging system with the perimeter 208 of tissue volume 206. By recalling the original size of tissue mass 200 and continually noting the location of perimeter 208 of the frozen tissue volume 206, it is possible to approximately determine when the size of the frozen tissue volume 206 is sufficiently large to provide the desired tissue margin 212. It is to be appreciated, however, that it is much more difficult to assess when tissue margins 212 of desired size have been achieved using this embodiment of the present method, then with the embodiments involving the use of system 8.

Following growth of the frozen tissue volume 206 to the desired dimensions, delivery of cooling fluid to cryoprobe 220 is terminated, and removal of the tissue volume commences. The latter is removed in the same manner tissue volume 206 is removed with the embodiment of the present method involving the use of system 8, as described above.

An important advantage of the present invention is that by freezing cryoprobe 220 to tissue volume 206, it is possible for the surgeon removing the tissue volume to easily and effectively stabilize the tissue volume. This greatly facilitates removal of tissue volume 206 insofar as the surgeon can readily identify the location and boundaries of the tissue volume. In amorphous and pliable tissue such as breast tissue, this ability to locate and define the dimensions of the tissue volume 206 to be removed, enhances significantly the likelihood that the entire tissue mass 200 is removed, while at the same time ensuring as little normal tissue is removed. That is, it helps ensure tissue margins 212 are as small as possible. In this era of tissue-conserving therapies, system 8 and the present method of stabilizing and removing tissue constitute an important advance in the art.

A related advantage of the present invention is that it permits a surgeon of ordinary ability to remove a tissue mass 200 in amorphous and pliable tissue with the same degree of precision and success as top surgeons in the field. Stabilization of tissue volume 206 using cryoprobe 220 provides location and dimension information with respect to the tissue portion that is quickly and easily accessible to the surgeon.

While the present invention has been described in connection with certain preferred embodiments, it will be understood that it is not limited to those embodiments. On the contrary, it is intended to cover all alternatives, modifications and equivalents as may be included within the spirit and scope of the invention as defined in the appended claims.

What is claimed is:

1. A method of stabilizing and removing a tissue volume having a perimeter, the method comprising the steps of:
   a. inserting a cryoprobe for freezing tissue in a tissue volume to be stabilized so that a portion of the cryoprobe projects from the tissue volume;
   b. freezing the tissue volume with the cryoprobe commencing with regions adjacent the cryoprobe and moving outwardly away from the cryoprobe;
   c. monitoring the temperature of the tissue volume adjacent a perimeter thereof during said freezing step;
   d. terminating said freezing step when said temperature reaches a first temperature level; and
   e. removing the tissue volume while grasping the cryoprobe so as to stabilize the tissue volume.

2. The method according to claim 1, further including the step, after said step d), of: continuing monitoring said temperature and providing an alarm signal when said temperature reaches a second temperature level.

3. The method according to claim 2, wherein said first temperature level is higher than said second temperature level.

4. The method according to claim 1, further including the step, after said step c), of monitoring the temperature in a tissue portion at a location radially outward of the perimeter during said freezing step, as measured from a central location in the tissue volume.

5. The method according to claim 4, further including the step of providing an alarm signal when said temperature of said tissue portion at said location reaches a third temperature level.

6. A method according to claim 1, wherein in said step c), said temperature monitoring includes the steps of:
   a. implanting a plurality of temperature sensors at or near the outer boundary, each of which has a unique identification code and provides a first signal containing information regarding the temperature of tissue adjacent thereto in response to receipt of a second signal containing an identification code that matches said unique identification code;
   b. generating said information with each sensor;
   c. iteratively interrogating said plurality of sensors with a plurality of second signals each having an identification code matching said unique identification code of one of said plurality of sensors; and
   d. detecting said first signal from each sensor, each first signal containing said unique identification code and said information for said each sensor.

7. A method according to claim 6, wherein said temperature monitoring step further includes the step of:
   a. displaying said temperature information for each sensor in a humanly recognizable representation.

* * * * *

UNITED STATES PATENT AND TRADEMARK OFFICE
CERTIFICATE OF CORRECTION

PATENT NO.   : 6,401,722 B1
DATED        : June 11, 2002
INVENTOR(S)  : David N. Krag It is certified that error appears in the above-identified patent and that said Letters Patent is hereby corrected as shown below:

<u>Title page,</u>
Item [56], References Cited, U.S. PATENT DOCUMENTS, "VaughAn" should read -- Vaughan --;

<u>Column 2,</u>
Line 30, add period after "frozen";

<u>Column 3,</u>
Line 64, "senor" should be -- sensor --;

<u>Column 4,</u>
Line 43, "using sensor" should be -- using a sensor --;

<u>Column 6,</u>
Line 42, "used the" should be -- used in the --;

<u>Column 9,</u>
Line 35, "may the" should be -- may be the --;

<u>Column 12,</u>
Line 12, "in a each" should be -- in each --;

Signed and Sealed this

Fourteenth Day of January, 2003

JAMES E. ROGAN
*Director of the United States Patent and Trademark Office*